(12) United States Patent
Maier et al.

(10) Patent No.: US 12,205,690 B1
(45) Date of Patent: *Jan. 21, 2025

(54) SYSTEMS AND METHODS FOR EXCLUDED RISK FACTOR PREDICTIVE MODELING

(71) Applicant: MASSACHUSETTS MUTUAL LIFE INSURANCE COMPANY, Springfield, MA (US)

(72) Inventors: Marc Maier, Springfield, MA (US); Shanshan Li, Springfield, MA (US); Hayley Carlotto, Springfield, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/119,654

(22) Filed: Mar. 9, 2023

Related U.S. Application Data

(63) Continuation of application No. 15/931,777, filed on May 14, 2020, now Pat. No. 11,694,775.

(Continued)

(51) Int. Cl.
*G16H 10/60* (2018.01)
*G06N 20/00* (2019.01)

(Continued)

(52) U.S. Cl.
CPC ............. *G16H 10/60* (2018.01); *G06N 20/00* (2019.01); *G16H 10/20* (2018.01); *G16H 20/10* (2018.01); *G16H 50/70* (2018.01)

(58) Field of Classification Search
CPC ........ G16H 10/60; G16H 10/20; G16H 20/10; G16H 50/70
See application file for complete search history.

(56) References Cited

U.S. PATENT DOCUMENTS

| | | |
|---|---|---|
| 8,521,568 B1 | 8/2013 | Easley |
| 11,257,574 B1 | 2/2022 | Boussios et al. |

(Continued)

FOREIGN PATENT DOCUMENTS

| | | |
|---|---|---|
| WO | WO-2015/084548 A1 | 6/2015 |
| WO | WO-2017/220140 A1 | 12/2017 |

OTHER PUBLICATIONS

Argys et al., Killer Debt: The Impact of Debt on Mortality, FRB Atlanta Working Paper No. 2016-14, (Nov. 1, 2016) (Year: 2016).*

(Continued)

*Primary Examiner* — Jonathan Ng
*Assistant Examiner* — Benjamin L. Hanks
(74) *Attorney, Agent, or Firm* — Foley & Lardner LLP

(57) ABSTRACT

A suite of fluidless predictive machine learning models includes a fluidless mortality module, smoking propensity model, and prescription fills model. The fluidless machine learning models are trained against a corpus of historical underwriting applications of a sponsoring enterprise, including clinical data of historical applicants. A data appended procedure supplements historical applications data with public records and credit risks. Various features of this data are engineered for improved predictive characteristics. Fluidless models are trained by application of a random forest ensemble including survival, regression and classification models. The trained models produce high-resolution, individual mortality scores. A fluidless underwriting protocol runs these predictive models to assess mortality risk and other risk attributes of a fluidless application that excludes clinical data to determine whether to present an accelerated underwriting offer. If any of the fluidless predictive models determines a high risk target, the applicant is required to submit clinical data.

20 Claims, 6 Drawing Sheets

Related U.S. Application Data

(60) Provisional application No. 62/993,584, filed on Mar. 23, 2020, provisional application No. 62/899,543, filed on Sep. 12, 2019, provisional application No. 62/848,397, filed on May 15, 2019.

(51) Int. Cl.
    *G16H 10/20* (2018.01)
    *G16H 20/10* (2018.01)
    *G16H 50/70* (2018.01)

(56) References Cited

U.S. PATENT DOCUMENTS

| | | |
|---|---|---|
| 2003/0037063 A1 | 2/2003 | Schwartz |
| 2003/0177032 A1 | 9/2003 | Bonissone et al. |
| 2007/0021987 A1 | 1/2007 | Binns et al. |
| 2009/0204446 A1 | 8/2009 | Simon et al. |
| 2009/0265190 A1 | 10/2009 | Ashley et al. |
| 2013/0173283 A1 | 7/2013 | Morse et al. |
| 2014/0172466 A1 | 6/2014 | Kemp et al. |
| 2015/0039351 A1 | 2/2015 | Bell et al. |
| 2015/0287143 A1 | 10/2015 | Gabriel et al. |
| 2015/0294420 A1 | 10/2015 | Hu |
| 2016/0048766 A1* | 2/2016 | McMahon ............ G06Q 40/08 706/12 |
| 2016/0078195 A1 | 3/2016 | Sarkar et al. |
| 2016/0196394 A1 | 7/2016 | Chanthasiriphan et al. |
| 2017/0124662 A1 | 5/2017 | Crabtree et al. |
| 2019/0180379 A1* | 6/2019 | Nayak .................... G06N 20/10 |
| 2019/0180852 A1* | 6/2019 | Jiao ........................ G16H 50/20 |
| 2019/0220793 A1 | 7/2019 | Saarenvirta |
| 2019/0378210 A1 | 12/2019 | Merrill et al. |
| 2020/0020040 A1 | 1/2020 | Gokhale et al. |
| 2020/0098048 A1 | 3/2020 | Kuruvilla et al. |
| 2020/0104876 A1 | 4/2020 | Chintakindi et al. |
| 2020/0160998 A1 | 5/2020 | Ward et al. |
| 2022/0391670 A1 | 12/2022 | Dalli et al. |

OTHER PUBLICATIONS

Aggour, K. S.; Bonissone, P. P.; Cheetham, W. E.; and Messmer, R. P. 2006. Automating the underwriting of insurance applications. AI magazine 27(3):36; Sep. 2006; 15 pages.

B. Letham, C. Rudin, T. H. McCormick, and D. Madigan; Interpretable classifers using rules and bayesian analysis: Building a better stroke prediction model. Annals of Applied Statistics; Apr. 2015; 22 pages.

Breiman, L. 2001. Random forests. Machine learning 45(1):5-32; Apr. 11, 2001; 11 pages.

Case, A., and Deaton, A. 2015. Rising morbidity and mortality in midlife among white non-hispanic Americans in the 21st century. Pmc. of the National Academy of Sciences 112(49): 15078-15083; Sep. 17, 2015; 6 pages.

Chen, T., and Guestrin, C. 2016. Xgboost: A scalable tree boosting system. In Proceedings of the Twenty-Second ACM SIGKDD In?ternational Conference on Knowledge Discovery and Data Mining, 785-794. ACM; Aug. 13, 2016; 10 pages.

Chokshi, D. A.; El-Sayed, A. M.; and Stine, N. W. 2015. J-shaped curves and public health. JAMA 314(13):1339-1340; Oct. 6, 2015; 2 pages.

Consumer Financial Protection Bureau. Consumer credit reports: A study of medical and non-medical collec?tions, https://files.consumerfinance.gov/f/201412 cfpb reports consumer-credit-medical-and-non-medical- collections.pdf, Dec. 2014; 53 pages.

Cox, D. R. 1972. Regression models and life-tables regression. Journal of the Royal Statistical Society, Series B 34:187-220; Mar. 8, 1972; 34 pages.

Cox, H. J.; Bhandari, S.; Rigby, A. S.; and Kilpatrick, E. S. 2008. Mortality at low and high estimated glomerular filtration rate values: A u-shaped curve. Nephron Clinical Practice 110(2):c67-c72; Feb. 19, 2008; 6 pages.

D. Sculley, Gary Holt, Daniel Golovin, Eugene Davydov, Todd Phillips, Dietmar Ebner, Vinay Chaudhary, Michael Young, Jean-Francois Crespo, and Dan Dennison. Hidden technical debt in machine learning systems. In Advances in Neural Information Processing Systems 28, pp. 2503-2511. 2015; Oct. 7, 2017; 9 pages.

David J Garrow. Toward a definitive history of Griggs v. Duke Power Co., Vand. L. Rev., 67:197, Jan. 22, 2014 41 pages.

Goldwasser, P., and Feldman, J. 1997. Association of serum albumin and mortality risk. Journal of Clinical Epidemiology 50(6):693-703; Feb. 3, 1997; 11 pages.

Guizhou Hu, Mortality Assessment Technology: A New Tool for Life Insurance Underwriting, On The Risk, vol. 18, No. 3, https://pdfs.semanticscholar.org/bac0/3b8a85bf89c7a7b65076c082632d2d325519.pdf, 2002, 9 pages.

Hemant Ishwaran, Udaya B Kogalur, Eiran Z Gorodeski, Andy J Minn, and Michael S Lauer. High-dimensional variable selection for survival data. Journal of the American Statistical Association, 105(489):205-217, Nov. 2008, 13 pages.

Hemant Ishwaran, Udaya B Kogalur, Eugene H Blackstone, and Michael S Lauer. Random Survival Forests. The Annals of Applied Statistics, 2(3):841-860; Mar. 2008, 22 pages.

John Karlen. climbeR: "Calculate Average Minimal Depth of a Maximal Subtree for 'ranger' Package Forests"; https://CRAN.R-project.org/package=climbeR. R package version 0.0.1, Nov. 19, 2016; 8 pages.

Kalben, B. B. 2000. Why men die younger: Causes of mortality differences by sex. N. Am. Actuarial Journal 4(4):83-111; Jan. 4, 2013; 30 pages.

Kaplan, E. L., and Meier, P. 1958. Nonparametric estimation from incomplete observations. Journal of the American Statistical Association 53(282):457-481; Jun. 1958; 25 pages.

Katzman, J.; Shaham, U.; Bates, J.; Cloninger, A.; Jiang, T.; and Kluger, Y. 2016. Deep survival: A deep cox proportional hazards network. arXiv preprint arXiv: 1606.00931; Jun. 2016; 11 pages.

Kronmal, R. A.; Cain, K. C.; Ye, Z.; and Omenn, G. S. 1993. Total serum cholesterol levels and mortality risk as a function of age: A report based on the Framingham data. Archives of Internal Medicine 153 (9):1065-1073; May 10, 1993; 9 pages.

Lipton, Z. C. 2016. The mythos of model interpretability. In Proceedings of the ICML Workshop on Human Interpretability in Machine Learning, 96-100; Jun. 10, 2016; 5 pages.

Lundberg, Scott M, Gabriel G Erion, and Su-In Lee.;"Consistent Individualized Feature Attribution for Tree Ensembles." arXiv Preprint arXiv:1802.03888.; Feb. 12, 2018; 9 pages.

Marc Maier, Hayley Carlotto, Freddie Sanchez, Sherriff Balogun, Sears Merritt; "Transforming Underwriting in the Life Insurance Industry"; Proceedings of the Thirty-Third AAAI Conference on Artificial Intelligence, vol. 33 (2019):; Jul. 17, 2019; 8 pages.

Mike Batty et al., Predictive Modeling for Life Insurance: Ways Life Insurance can participate in the Business Analytics Revolution, Deloitte Consulting LLP, Apr. 2010, 22 pages.

National Association of Insurance Commissioners. Credit-based insurance scores, 2018. https://www.naic.org/cipr topics/topic credit based insurance score.htm , last updated Dec. 7, 2018, 3 pages.

Peter WF Wilson, Ralph B D'Agostino, Daniel Levy, Albert M Belanger, Halit Silbershatz, and William B Kannel. Prediction of coronary heart disease using risk factor categories. Circulation, 97(18):1837-1847, May 1998; 11 pages.

Phillip Janz et al., "The Impact On Relative Mortality and Prevalence from Triage in an Accelerated Underwriting Program", Reinsurance News, Jul. 2019, 5 pages.

Ranganath, R.; Perotte, A.; Elhadad, N.; and Blei, D.; Deep survival analysis. arXiv preprint arXiv: 1608.02158; Aug. 6, 2016; 13 pages.

Ribeiro, M. T.; Singh, S.; and Guestrin, C.; Why should I trust you?: Explaining the predictions of any classifier. In Proceedings of the Tventy-Second ACM SIGKDD International Conference on Knowledge Discovery and Data Mining, 1135-1144. ACM; Feb. 16, 2016; 10 pages.

Richard Wright, Mark Ellis, Steven R Holloway, and Sandy Wong. Patterns of racial diversity and segregation in the united states: 1990-2010. The Professional Geographer, 66(2):173-182, https://europepmc.org/articles/pmc4114976, Jan. 2013; 17 pages.

(56) References Cited

OTHER PUBLICATIONS

Robert Chen et al., "Patient Stratification Using Electronic Health Records from a Chronic Disease Management Program", IEEE J Biomed Health Inform., Author manuscript; available in PMC Jul. 4, 2017.

Ronen Avraham, Kyle D Logue, and Daniel Schwarcz. Understanding insurance antidiscrimination law. S. Cal. L. Rev., 87:195, Jan. 2014; 81 pages.

Rosinger, A.; Carroll, M. D.; Lacher, D.; and Ogden, C. 2017. Trends in total Cholesterol, Triglycerides, and Low-density Lipoprotein in US Adults, 1999-2014. JAMA Cardiology 2(3):339-341; Mar. 2017; 3 pages.

Scism, L. 2017. New York regulator seeks details from life insurers using algorithms to issue policies. The Wall Street Journal; Jun. 29, 2017; 2 pages.

Scott M Lundberg and Su-In Lee. A unified approach to interpreting model predictions. In I. Guyon, U. V. Luxburg, S. Bengio, H. Wallach, R. Fergus, S. Vishwanathan, and R. Garnett, editors, Advances in Neural Information Processing Systems 30, pp. 4765-4774. Curran Associates, Inc., http://papers.nips.cc/paper/7062-a-unified-approach-to-interpreting-model-predictions.pdf, May 22, 2017; 10 pages.

Wright, M. N., and Ziegler, A. 2017. ranger: A fast implementation of random forests for high dimensional data in C++ and R. Journal of Statistical Software 77(1): Mar. 1-17, 2017; 17 pages.

\* cited by examiner

SYSTEMS AND METHODS FOR EXCLUDED RISK FACTOR PREDICTIVE MODELING

CROSS-REFERENCE TO RELATED APPLICATIONS

The present application is a continuation of U.S. Ser. No. 15/931,777, entitled "SYSTEMS AND METHODS FOR EXCLUDED RISK FACTOR PREDICTIVE MODELING," filed May 14, 2020, which claims benefit of U.S. Provisional App. No. 62/848,397, filed May 15, 2019, claims the benefit of U.S. Provisional App. No. 62/899,543, filed Sep. 12, 2019, and claims the benefit of U.S. Provisional App. No. 62/993,584, filed Mar. 23, 2020, all of which are incorporated by reference in their entirety.

TECHNICAL FIELD

The present disclosure relates generally to underwriting of insurance based on predictive modeling of mortality risk factors, and more particularly to underwriting applications for insurance based on predictive modeling with excluded mortality risk factors.

BACKGROUND

Many financial service companies and other enterprises require health information from consumers for underwriting. Traditionally, the customers may be presented an initial questionnaire, which typically asks general questions related to age, weight, medical history, and the like. However, the customers may need to undergo medical examinations, which typically involve collecting body fluids and different physical measurements. Collecting such data is often a problem for the customers for a variety of physical and/or psychological reasons and can be a major barrier to financial service companies and other enterprises attempting to underwrite insurance products or otherwise enroll new customers. More particularly, the consumers often do not want to have blood drawn for fear of needles, do not want to undergo medical screening, do not have the time, and many other reasons.

The problems associated with transfer and pooling of risk are integral elements in the operation of life insurance systems. By grouping individuals' risk, the insurance systems are able to cover losses based on possibly future arising risks out of a common pool of resources captured by the insurance systems. However, in order to maintain some degree of equity among individuals exhibiting different mortality risks, the insurance systems must capture, assess and classify risk of applicants for life insurance according to appropriate criteria or risk factors. Traditional underwriting practice has been to require applicants for life insurance to undergo medical examinations, including collection of body fluids and various physical measurements, and analysis of risk factors based on these inputs. In the present disclosure, these risk factors based on collection of body fluids and various biophysical measurements are sometimes clinical assessment risk factors.

What is needed is improved methods for predictive modeling of mortality for applicants for financial products such as life insurance that treat clinical assessment risk factors as excluded risk factors. What is needed is accelerated methods for underwriting of applications of financial products such as life insurance, without collection and analysis of body fluids and various biophysical measurements as inputs.

SUMMARY

Embodiments described herein aim to improve customer experience with faster processing and reduced customer burdens of providing information required by the underwriting process. A fluidless underwriting protocol eliminates the traditional requirement in underwriting of life insurance products of collecting body fluids and various physical measurements and analyzing risk factors based on these inputs. Improved systems and methods for predictive modeling of mortality treat clinical assessment data as excluded risk factors while enabling assessment and classification of risk with respect to applicants for life insurance according to acceptable alternative criteria.

In various embodiments, a processor-based method executes a first predictive machine learning model configured to determine a mortality risk score for each historical application record of a plurality of historical application records including clinical assessment data. This method inputs the historical application records into a machine learning model ensemble utilizing one or more of survival modeling, regression modeling, and classification modeling. In various embodiments, the machine learning model ensemble uses random forest methods.

In an embodiment, each of the plurality of historical application records includes clinical assessment data for an applicant of the respective historical application record. Prior to inputting the historical application records into the machine learning model ensemble, the method supplements each historical application record with public data identified with the applicant of the respective historical application record. As described herein, the method appends to each historical application record public data identified with the applicant of the respective historical application record. In an embodiment, the public data comprises public records and credit risk data. In various embodiments, the first predictive machine learning model is continuously trained using updated public records and credit data.

In an embodiment, upon receiving an application from a user display device that omits clinical assessment data for the applicant, the fluidless underwriting method processes the application to determine whether to present an accelerated underwriting offer or to require the applicant to submit clinical data. The method retrieves public data identified with the applicant of the fluidless application, then runs the first predictive machine learning module to determine a mortality risk score. In an embodiment, the public data comprises public records and credit risk data. Based on the mortality risk score, the fluidless mortality model classifies the fluidless application into one of a first high risk group and a first low risk group.

Additionally, the fluidless underwriting protocol runs a second predictive machine learning module to determine a second risk rank representative of a second user risk attribute. Based upon the second risk rank, the protocol classifies the fluidless application into one of a second high risk group and a second low risk group. The fluidless underwriting protocol also runs a third predictive machine learning module to determine a third risk rank representative of a third user risk attribute. Based upon the third risk rank, the protocol classifies the fluidless application into one of a third high risk group and a third low risk group. In an embodiment, the second user risk attribute and the third user risk attribute each predict likelihood of at least one additional risk factor that normally can be indicated by clinical data when included in an application.

In various embodiments, in the event the protocol classifies the fluidless application into all of the first low risk group, the second low risk group, and the third low risk group, a display device in communication with the processor displays an accelerated application offer. In the event the protocol classifies the fluidless application into at least one of the first high risk group, the second high risk group, or the third high risk group, a display device in communication with the processor displays an instruction to submit clinical assessment data for the applicant of the fluidless application.

In an embodiment, a method, comprises receiving, by a server, information for an electronic application to an enterprise from a user device, wherein the information for the electronic application excludes clinical data for an applicant; retrieving, by the server, upon receiving the information for the electronic application from the user display device, public data identified with the applicant of the electronic application from one or more third party sources; executing, by the server, a first predictive machine learning module configured to determine a first risk rank representative of a mortality risk for the electronic application and to classify the electronic application into one of a first high risk group and a first low risk group based upon the first risk rank, wherein the first predictive machine learning module comprises a machine learning model ensemble utilizing one or more of survival modeling, regression modeling, and classification modeling trained by inputting into the first predictive machine learning module a plurality of historical application records of the enterprise wherein each historical application record is supplemented with public data identified with an applicant of the respective historical application record received from the one or more third party sources; executing, by the server, a second predictive machine learning module configured to determine a second risk rank representative of a smoking propensity of the electronic application and to classify the electronic application into one of a second high risk group and a second low risk group based upon the second risk rank; executing, by the server, a third predictive machine learning module configured to determine a third risk rank representative of prescription drug data of the electronic application, and to classify the electronic application into one of a third high risk group and a third low risk group based upon the third risk rank; and in the event the server classifies the electronic application into all of the first low risk group, the second low risk group, and the third low risk group, presenting, by the server, a user interface that displays information associated with an accelerated application offer.

In another embodiment, a processor-based method comprises executing, by a processor, a first predictive machine learning model configured to determine, for each historical application record of a plurality of historical application records stored in a database of an enterprise, a mortality risk rank by inputting the historical application records supplemented by public records and credit risk data identified with an applicant of the respective historical application record received from one or more third party sources into a machine learning model ensemble comprising random forest models utilizing one or more of survival modeling, regression modeling, and classification modeling, wherein feature selection for the first predictive machine learning model excludes clinical risk assessment attributes of the historical application records, and selects actuarially important attributes of the public records and credit risk data as covariates of the first predictive machine learning model; and upon receiving information for an electronic application to the enterprise from a user device, wherein the information for the electronic application excludes clinical data for an applicant of the electronic application: retrieving, by the processor, public records and credit risk data identified with the applicant of the electronic application; executing, by the processor, the first predictive machine learning module to determine a mortality risk score, and to classify the electronic application into one of a first high risk group and a first low risk group based upon the mortality risk score; executing, by the processor, a second predictive machine learning module to determine a second risk rank representative of a second user risk attribute, wherein the second risk attribute predicts likelihood of at least one risk factor that can be indicated by clinical data; and to classify the electronic application into one of a second high risk group and a second low risk group based upon the second risk rank; and in the event the processor classifies the electronic application into the first low risk group and the second low risk group, presenting a user interface that displays information associated with an accelerated application offer.

In a further embodiment, a system comprises an analytical engine server comprising a first module configured for receiving information for an electronic application from a user device that excludes clinical data for an applicant of the electronic application, and for retrieving public data identified with the applicant of the received electronic application from one or more third party sources; a second module configured for executing a predictive machine learning module to determine a mortality risk rank for the electronic application and classify the electronic application into a first low risk group or a first high risk group, wherein the predictive machine learning module comprises a machine learning model ensemble utilizing one or more of survival modeling, regression modeling, and classification modeling trained by inputting into the predictive machine learning module a plurality of historical application records of the enterprise wherein each historical application record is supplemented with public data identified with an applicant of the respective historical application record received from the one or more third party sources; a third module configured for executing a smoking propensity predictive model, wherein the smoking propensity model is configured to estimate a propensity of the applicant of the electronic application to be a smoker and determine a smoking/non-smoking binary target; a fourth module configured for executing a prescription drug data predictive model configured to determine disqualifying medical risks based on information derived from prescription drug fills for the applicant of the electronic application; and a fifth module configured for generating and presenting a user interface that displays information associated with an accelerated application offer in the event the analytical engine server classifies the electronic application into the first low risk group, determines the non-smoking binary target, and does not determine the disqualifying medical risk.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

DETAILED DESCRIPTION

Figure 1:
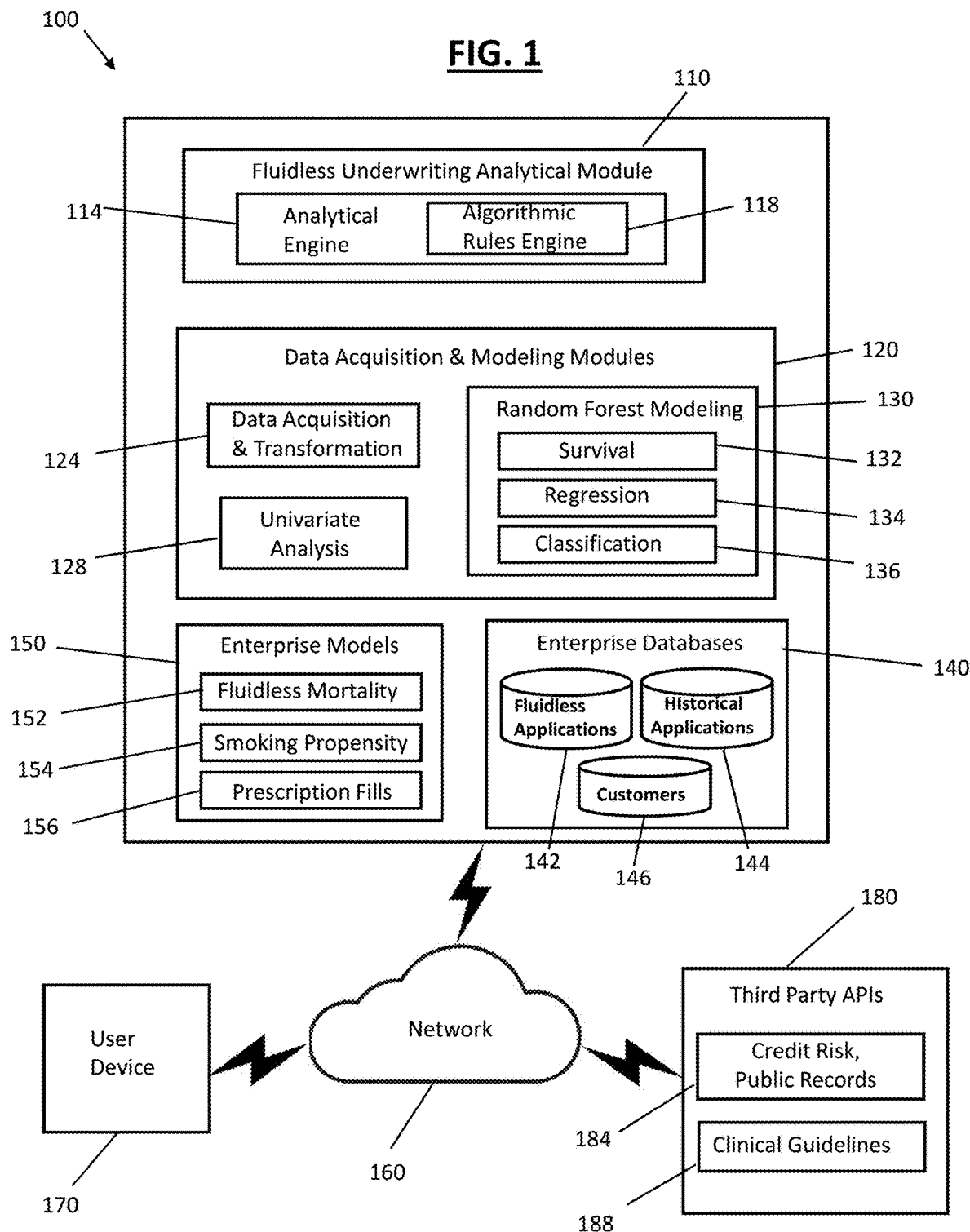
FIG. 1 is a system architecture for a fluidless underwriting system of an enterprise, according to an embodiment.

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following.

Underwriting is the process an insurance company uses to determine whether or not a potential customer is eligible for insurance, and what rate that potential customer should pay for the insurance if eligible. Insurance underwriting seeks to spread risk among a pool of insured in a manner that is both fair to the customer and profitable for the insurer. One consideration is that it does not make sense for insurers to sell life insurance, for example, to everyone who applies for it. Additionally, although insurance companies do not intend to charge their customers excessively high rates, it is not prudent for them to charge all their policyholders the same premium. Underwriting enables the company to decline coverage to certain applicants, and to charge the remaining applicants premiums and to provide other policy terms that are commensurate with their level of risk.

Traditionally, most types of life insurance require an estimate of the expected lifetime of an individual at the time of application, commonly called the mortality risk. Conventional protocols for collecting and analyzing data that describes mortality risk are known as underwriting. Actuaries compute the cost of covering mortality risk over the lifetime of the policy and translate it into a set of premium payments required throughout a policy's term. Life insurance risk assessment has primarily consisted of point systems developed by medical doctors and experienced underwriters. Such protocols commonly calculate risk by mapping medical and behavioral attributes to point values that either debit or credit an overall score. A life underwriter reviews an application to calculate the net number of points and to determine one of several risk classes that determine pricing according to aggregate mortality.

Traditionally, underwriting has been a manual process. Underwriting can involve numerous people including agents and doctors, and it can be very time-consuming. Therefore, various entities have developed systems and methods to automate the underwriting process in order to improve decision-making, reduce the number of people involved, and accelerate the underwriting process. These systems and methods may be referred to as algorithmic underwriting.

The system and method of the present disclosure represent an underwriting protocol that improves customer experience with faster processing and reduced customer burdens of providing information required by the underwriting process. In various embodiments, the underwriting protocol eliminates the traditional requirement in underwriting of life insurance products of collection of body fluids and various physical measurements, and analysis of risk factors based on these inputs. In the present disclosure, the underwriting protocol and the application received from the user are sometimes called "fluidless" (e.g., fluidless underwriting, fluidless application).

As used in the present disclosure, a "risk factor" is any variable associated with a health outcome or state, such as a risk of disease, infection and/or health-related event, e.g., a stroke, diabetes, heart attack, cancer and death. Risk factors may be correlated with a health outcome or state and may or may not, have a causal relationship with a health outcome or state. In the present disclosure, the omitted or excluded risk factors are risk factors derived from collection and analysis of body fluids and various biophysical measurements. In the present disclosure, these are sometimes called "clinical assessment risk factors" or alternatively "clinical assessments," and the collected medical data for these clinical assessments (e.g., body fluids and biophysical measurements) are sometimes called "clinical data," or alternatively "clinical laboratory data."

In lieu of clinical assessments as inputs to mortality predictions, the system and method of the present disclosure employ a mortality predictive model trained using data from a large corpus of historical applications based on traditional underwriting protocols, in conjunction with public data sources that can provide a thorough view of prospective customers. In various embodiments, the system and methods of the present disclosure receive as input applications of prospective customers that exclude clinical data, and apply fluidless mortality predictive modeling to determine whether to approve sale to the applicant of a risk-pooling product, such as life insurance. In various embodiments, if the fluidless underwriting protocol does not result in approval of the fluidless application, the applicant can submit clinical data in an application to be underwritten inclusive of those risk factors.

Clinical data collected in medical examinations in support of conventional applications for life insurance are typically employed to assess the applicant's health, to confirm information included in the application, and to screen for illegal drug use. Much of the collected clinical data is also obtained from other sources during the application process, and clinical test results and answers to examination questions are typically checked for consistency with the other sources.

Clinical laboratory data are a point-in-time view into an individual's health. Underwriting ties various clinical data to all-cause mortality predictions and to specific causes of mortality. Clinical assessments based on collected blood and urine samples typically test the collected fluids to screen for dozens of indicators of diseases and conditions (health indicators). Examples of clinical assessment risk factors include HIV and AIDS; sexually transmitted diseases (STD); cholesterol, (including LDL and HDL) and triglycerides (e.g., as indicators of heart disease risk factors); hemoglobin A1C, fructosamine and glucose levels (e.g., as indicators of diabetes); creatinine, hemoglobin and proteins (e.g., as indicators of kidney disease); and urine acidity (e.g., as indicator of impaired kidney function or diabetes). Typical medical examinations also screen for nicotine and cotinine in the urinalysis in order to determine tobacco usage. Additionally, clinical assessments may include biophysical examinations such as weighing the applicant and questioning the applicant, e.g., about lifestyle.

While excluding such clinical assessments eliminates informative indicators of risk factors that can yield substantial protective value in risk selection, the fluidless underwriting protocols of the present disclosure identify low-risk applicants for whom traditional clinical assessments can be waived with little to no impact on mortality risk. In lieu of clinical laboratory data, fluidless underwriting protocols disclosed herein utilize nontraditional data sources public records and credit risk that yield information on insurance applicants' behavior providing significant insights into mortality risk. In an embodiment, in addition to those nontraditional data sources, fluidless underwriting protocols disclosed herein include a client medical interview in the application process.

In an embodiment, a fluidless underwriting protocol was validated by simulating a set of applications approved by the protocol, also herein called a book of business. The simulation compared the book of business with historical underwriting risk class offers that effectively control all primary actuarial factors. This simulation showed that fluidless underwriting protocols incorporating the excluded risk-factor predictive modeling systems and methods of the present disclosure generate substantially improved offer rates based on accelerated underwriting without compromising mortality margins of conventional underwriting protocols.

In various embodiments, a fluidless underwriting method of the present disclosure applies, on demand, a fluidless mortality predictive model that has been trained against a large corpus of historical underwriting applications including clinical assessment data. During model training the method executes a predictive machine learning model configured to determine a mortality score for each historical application record of a plurality of historical application records stored in a historical application database. The method effects feature transformations on various attributes of historical application records to construct engineered features with improved impacts on predicted value. Additionally, the predictive machine learning model effects a missingness procedure that provides imputed values for missing values in the historical application data. The predictive machine learning model is configured to determine the set of mortality scores by inputting engineered features and the customer profile data into a suite of predictive models based on survival, regression, and classification tasks. In an embodiment, this suite of models uses the random forest algorithm.

FIG. 1 shows a system architecture for a fluidless application review system 100, also herein called fluidless underwriting system, of a sponsoring enterprise. The fluidless underwriting system 100 may be hosted on one or more computers (or servers), and the one or more computers may include or be communicatively coupled to one or more databases. The application review system 100 manages predictive modeling of mortality risk factors that exclude clinical assessment risk factors for applicants for life insurance or other financial products of the sponsoring enterprise.

In an embodiment, a sponsoring enterprise for fluidless application review system 100 is an insurance company or other financial services company, which may be represented by insurance agents or advisors. In some cases, an insurance agent may be associated with only a single insurance provider (sometimes referred to as a "captive" insurance agent). In other cases, an "independent" insurance agent, sometimes called an insurance broker, may be associated with several different insurance providers. In various embodiments, a user (customer or customer representative) submits a digital application via user device 180, and the digital application received by fluidless application review system 100 is assigned to an agent or advisor.

Fluidless underwriting analytical module 110 includes an analytical engine 114 and an algorithmic rules engine submodule 118. In an embodiment, algorithmic rules engine submodule 118 executes thousands of automated rules encompassing health, behavioral, and financial attributes collected through digital fluidless applications 142 and through real-time vendor APIs 180.

Analytical engine 114 can be executed by a server, one or more server computers, authorized client computing devices, smartphones, desktop computers, laptop computers, tablet computers, PDAs and other types of processor-controlled devices that receive, process, and/or transmit digital data. Analytical engine 114 can be implemented using a single-processor system including one processor, or a multi-processor system including any number of suitable processors that may be employed to provide for parallel and/or sequential execution of one or more portions of the techniques described herein. Analytical engine 114 performs these operations as a result of central processing unit executing software instructions contained within a computer-readable medium, such as within memory. In one embodiment, the software instructions of the system are read into memory associated with the analytical engine 114 from another memory location, such as from a storage device, or from another computing device via communication interface. In this embodiment, the software instructions contained within memory instruct the analytical engine 114 to perform processes described below. Alternatively, hardwired circuitry may be used in place of, or in combination with, software instructions to implement the processes described herein. Thus, implementations described herein are not limited to any specific combinations of hardware circuitry and software.

Enterprise databases 140 consists of various databases under custody of a sponsoring enterprise, including fluidless applications database 142, historical applications database 144, and customer database 146. Enterprise databases 140 are organized collections of data, stored in non-transitory machine-readable storage. In an embodiment, the databases may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of databases. The databases may conform to a well-known structural representational model, such as relational databases, object-oriented databases, and network databases. Example database management systems include MySQL, PostgreSQL, SQLite, Microsoft SQL Server, Microsoft Access, Oracle, SAP, dBASE, FoxPro, IBM DB2, LibreOffice Base, FileMaker Pro. Example database management systems also include NoSQL databases, i.e., non-relational or distributed databases that encompass various categories: key-value stores, document databases, wide-column databases, and graph databases.

A suite of fluidless models 150 includes a Fluidless Mortality Model 152, a Smoking Propensity Model 154, and a Prescription Fills Model 156. In various embodiments, fluidless models 150 were trained against a large corpus of historical underwriting applications 144 of a sponsoring enterprise. Data acquisition and transformations module 124 applied a data append procedure and data transformation procedures to the historical application data to yield an extensive data set with engineered features having improved predictive values. Fluidless models 150 were then trained by application of models within random forest survival models ensemble 130. Model training curated a data set on the scale of one million historical applications, wherein the historical applications included then-current clinical assessment data of the applicants. The trained models produced high-resolution, individual mortality scores.

In an embodiment, historical applications 144 included data obtained from an extended time period. This presented the challenge in modeling of taking into account temporal factors, such as a decreasing trend of certain lab values over the time period of the historical applications. In an embodiment, the modeling techniques of the disclosure applied a statistical adjustment to account for covariate shift or non-stationarity, i.e., differences in distribution of certain predictive variables over the relevant time period.

In various embodiments, model outputs of fluidless models 150 include risk scoring information, also herein called risk ranks. Risk ranks may include, for example quantitative risk scores, percentiles, binary risk outcomes, and risk classes. In an embodiment, risk ranks include the user's percentile within the score distribution for a population of general users, together with the score of the particular user. In an embodiment, risk scoring is a binary outcome, such as "pass" or "fail." In an embodiment, risk scores define one or more bins as percentile ranges in a percentile distribution for a population of general users. In an embodiment, risk scoring ranks cases by the likelihood of belonging to one risk class or the other. In an embodiment, risk scoring determines a quantitative risk score, such as net number of points, for the user and translates this risk score into one of several coarse-grained risk classes. In various embodiments, risk ranks include a risk class to which the user has been assigned. For example, the user may be assigned to UPNT for non-smokers or SPT for self-reported smokers.

Figure 2:
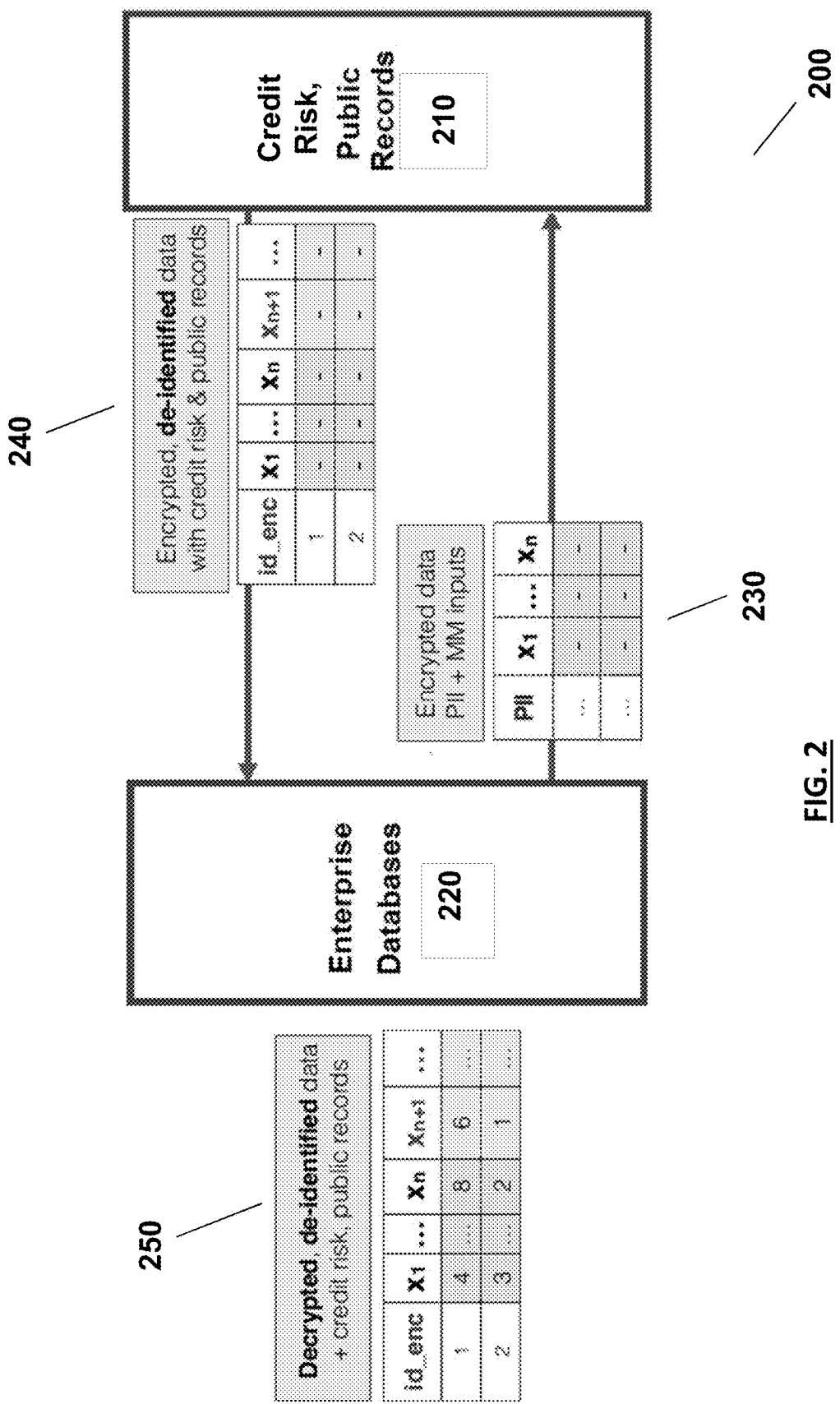
FIG. 2 illustrates a method for appending public records and credit risk data to historical application records, according to an embodiment.

FIG. 2 is a schematic diagram of a data acquisition and transformation procedure used to extract and transform historical applications data for historical insurance applicants of the enterprise, stored in Enterprise Databases 220. In an embodiment, the procedure of FIG. 2 was used to acquire appended applications data for the historical applications database 146 of FIG. 1, and to transform that data via data transformation module 128. Procedure 200 acquires historical applications data and supplements that data with non-traditional data using techniques that protect privacy rights of the applicants. Appended applications data includes non-traditional data attributes that supplement traditional underwriting attributes previously tracked by the enterprise for these historical applicants. In an embodiment, a third party data vendor of Credit Risk/Public Records databases 210 used personally identifiable information to match data 230 to internal records. Subsequently, the third party database vendor removed the personally identifiable information prior to returning the data set to the sponsoring enterprise at 240 with credit risk and public records attributes appended. At the final stage at 250, the data set in Enterprise Databases 220 was decrypted, and had a de-identified state to protect the privacy of customers.

Figure 3:
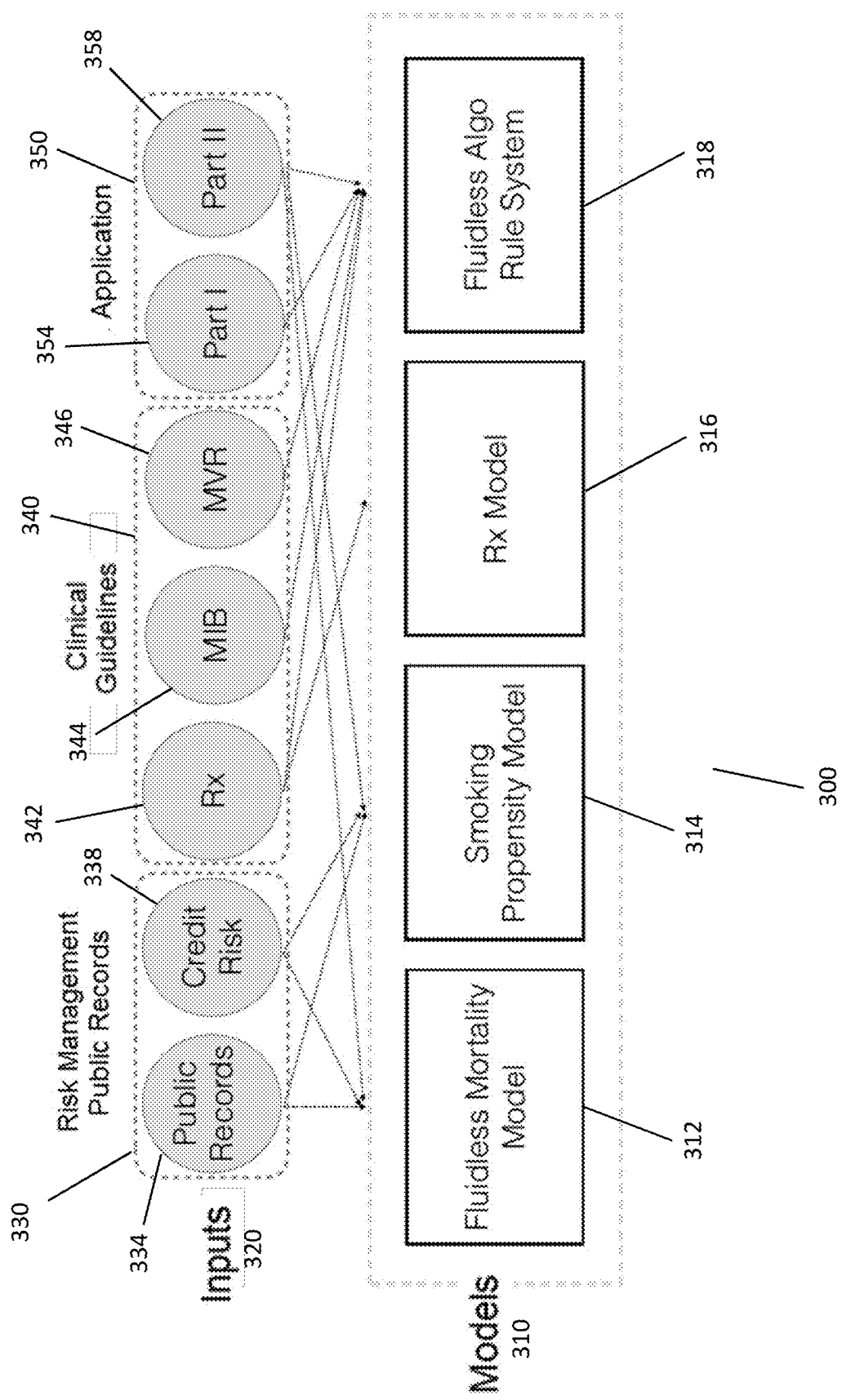
FIG. 3 is a schematic diagram of input data sources and models of a fluidless underwriting method, according to an embodiment.

In an embodiment, the fluidless model suite of Data Acquisition and Modeling Modules 120 acquires data from four primary data sources in modeling via data acquisition and transformation module 124. FIG. 3 shows a simplified schematic of a system 300 for evaluating program-eligible applicants for approval to receive a fluidless underwriting offer. Data sources of system 300 include two nontraditional underwriting sources, public records 334 and credit risk data 338, and two traditional underwriting sources, client medical interviews ("CMI"; application part II 355), and prescription drug histories (Rx data 342). As used in the present disclosure, the generic term "public data" denotes data relating to applicants of the enterprise obtained from one or more third party sources, and encompasses both "public records" and "credit risk data."

In various embodiments, "public records" include attributes that pertain to individual-level records that are filed by a public office, such as addresses, education, licenses, property, assets, and financial disclosures. Example public records attributes include the number of lien records on file, time since the most recent bankruptcy filing, number of evictions, and the tax-assessed value of the individual's current address. In an embodiment, public records data set 334 is acquired via third party API 184. In an embodiment, in preparation for model training this data was acquired via the data appended procedure 200 of FIG. 2. In an embodiment, in production this information is retrieved in real-time through API calls to a third party vendor of Public Records database 334.

In various embodiments, "credit risk data" include attributes with information that pertains to credit behavior, such as types of open accounts, account balances, derogatory remarks, collections, and bankruptcies. Example credit risk data attributes include the number of collections, ratio of amount past due to amount of total balances, and number of open auto finance accounts. In an embodiment, credit risk data set 338 is acquired via third party API 184. In an embodiment, in preparation for model training this data was acquired via the data append procedure 200 of FIG. 2. In an embodiment, in production this information is retrieved in real-time through API calls to a third party vendor of Credit Risk database 338.

The CMI data set 355 consists of an extensive questionnaire filled out by life insurance applicants. This digital questionnaire covers personal and family health history, and behavioral topics. In an embodiment, behavioral topics include motor vehicle violations, smoking, and other topics pertaining to behavioral risks. During model development, non-digital questionnaire responses were digitized, and data transformation procedures were applied to generate features that were incorporated into the model suite 310. In an example, the resulting training data included over 400 columns including both Boolean answers and keyword extraction on open-text fields that align to major medical impairments. In production, digital CMI data 355 and Application Part I data 354 is received via user inputs at user device 170, transmitted via network 160 and stored in fluidless applications database 142. Alternatively, this data is received via paper application and is digitized for storage.

In an embodiment, prescription drug histories data (Rx 342) contains historical prescription drug fills for applicants. In an embodiment, Rx 342 contains a 7-year history per applicant. In an embodiment, each fill record includes the drug generic name, brand name, NDC (National Drug Code), priority, days' supply, quantity, prescription fill date, physician name, registration number, and specialty. In an example, the Rx data set constructed during model building contained data for thousands of applicants, including more millions of prescription fill records. In an embodiment, in production the Rx data is collected in real-time via API calls to one or more third party vendors of online computer databases of medical prescription records.

Figure 4:
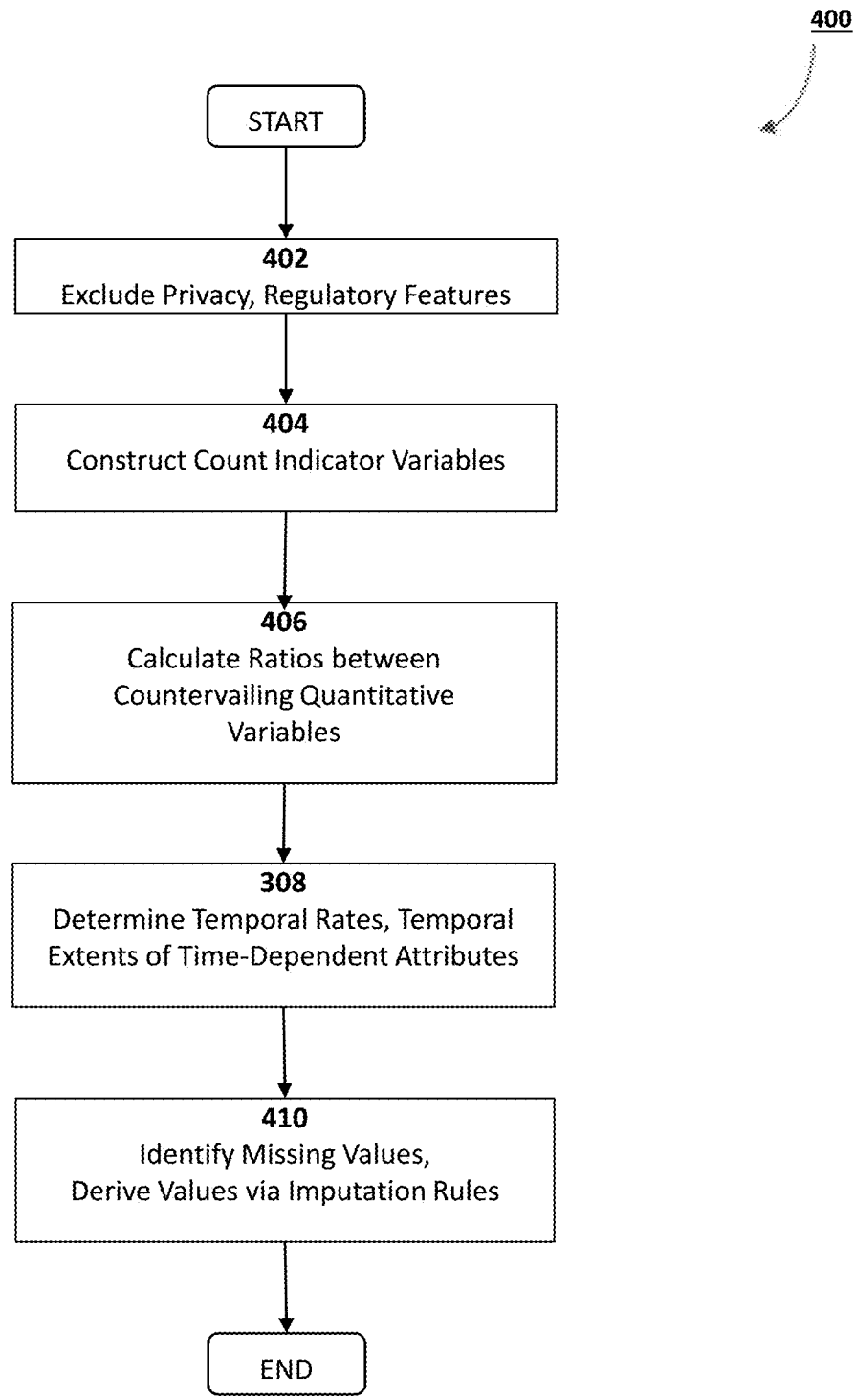
FIG. 4 is a flow chart diagram of data preprocessing procedures of a predictive machine learning module, according to an embodiment.

In an embodiment shown in the flow chart schematic of FIG. 4, during model development data acquisition and transformation module 124 applied various data pre-processing procedures 400 to acquired data. Step 402 excluded various certain features based on privacy or regulatory considerations and other factors.

Feature engineering procedures 404, 406, and 408 combined or otherwise transformed data attributes in various way to construct engineered variables that were potentially more useful in modeling. For example, in the medical literature, body-mass index (BMI) has been shown to be a more directly causal driver of mortality risk than weight (and especially height) alone. An example of an engineered variable is BMI as a function of height and weight, which addressed the significant interaction between height and weight. In various embodiments, engineered variables also were constructed for credit risk and public records attributes.

In an embodiment, data transformation procedures generated various classes of engineered features: indicators, ratios, and temporal rates. Step 404 constructed count indicator variables. This procedure addressed variables that are measured as a count (e.g., number of felonies) that have a very high proportion of zeros, with a very infrequent but long tail. Feature engineering constructed several indicator variables that reflect any non-zero count of such events.

Step 406 calculated ratios between countervailing quantitative variables. Developing ratios between counts of countervailing quantities can be useful to compute for statistical efficiency. In an embodiment, liens to properties is a weighted ratio of the number of filed or released liens to the number of owned properties (e.g., houses, aircrafts). This ratio was highly predictive in a fluidless mortality model 152 that relied on public records and CMI (application part II 355) as modeling inputs.

Step 408 determined temporal rates and temporal extents of time-dependent attributes. The credit risk and public records attributes often denote counts of quantities within certain temporal extents. As presented, these attributes are overlapping and highly correlated. This procedure develops features that represent rates of change across different durations (kinematics), such as measurements of actual change, velocity, and acceleration. Example time-dependent attributes include the number of non-derogatory accounts that are provided within the past 3 months, 6 months, 12 months, 24 months, and 60 months. From these attributes, step 408 can compute, for example, the velocity of non-derogatory accounts from 5 years to 2 years ago as the difference between the counts at those time periods divided by the 3-year duration.

Step 410 identified missing values in the acquired data, and derived substitute values for many of the missing values via imputation rules. In an embodiment, missing values were pervasive across the credit risk and public records attributes. In an embodiment of missingness procedure 410, the procedure was designed to avoid adverse impact to any individual score without knowledge of an observed value. In other words, the resulting model score should not be beneficial or detrimental to a given applicant with respect to similar applicants, if an unobserved value is passed as a model input.

In view of these objectives, missingness procedure 410 systematically imputed the median, mode, or a default value conditioned on an applicant's cohort as observed in the training data. A median was imputed if the variable was continuous, a modal value if categorical, and a default setting if specified in provided data dictionaries. During model training, the procedure sampled with replacement from observed values either with a median or modal value depending on variable type. Additionally, for continuous variables, the procedure avoided sampling from the 10% extreme of the tails to avoid over-representing outlying values.

Given an understanding of the acquired data set and of missingness associated with each source, model training of the enterprise models 150 employed univariate analysis 128 of the statistical association between individual attributes and the target outcomes of interest. FIGS. 5A-5D show several examples of this univariate analysis. It should be understood that the charts of FIGS. 5A-5D are disclosed only as illustrative examples of using observations in historical data as a basis for building multivariate models.

Figure 5A:
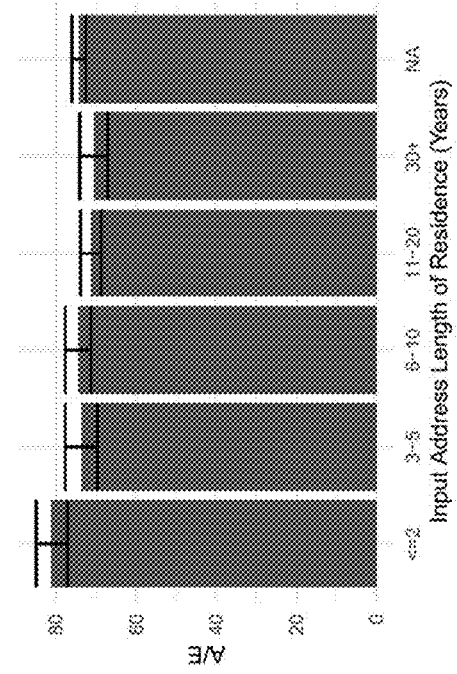
FIG. 5A displays a relationship between an individual's number of collections and input address length of residence, according to an embodiment.
Figure 5B:
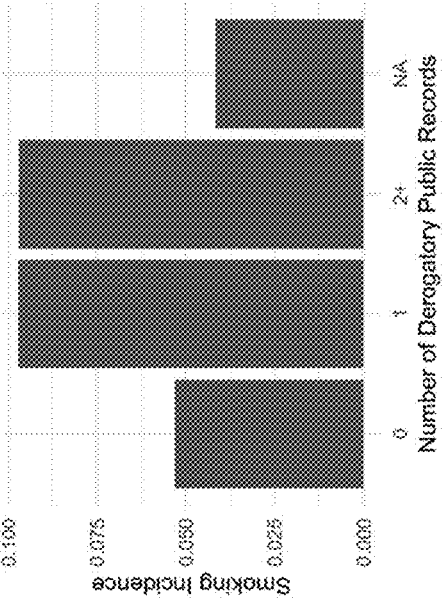
FIG. 5B displays a relationship between an individual's number of collections and input address length of residence, according to an embodiment.

FIG. 5A and FIG. 5B display the relationship between an individual's number of collections (medical and utility excluded) and input address length of residence with survival, as measured by the actual-to-expected (A/E) ratio. The A/E ratio compares the actual number of deaths with the expected number of deaths conditioned on the age, sex, duration of observation, and smoking status makeup of the underlying individuals. A low A/E signifies a low-risk set of individuals, while an A/E of 100% indicates that the expected number of individuals have died. Underwriting protocols aim to stratify a population, here life insurance applicants, to produce pools of risk with target A/E values that determine premiums. In FIG. 5A, number of collections (excluding medical and utility) have a monotonically increasing effect on mortality with 0 collections being associated with an A/E of 65.8% and 3 or more collections with an A/E of 110.9%. In FIG. 5B, input address length of residence has a negative relationship with mortality. A length of residence less than or equal to 2 years is associated with an A/E of 80.9% and a length of residence of more than 30 years has an A/E of 70.4%.

Figure 5C:
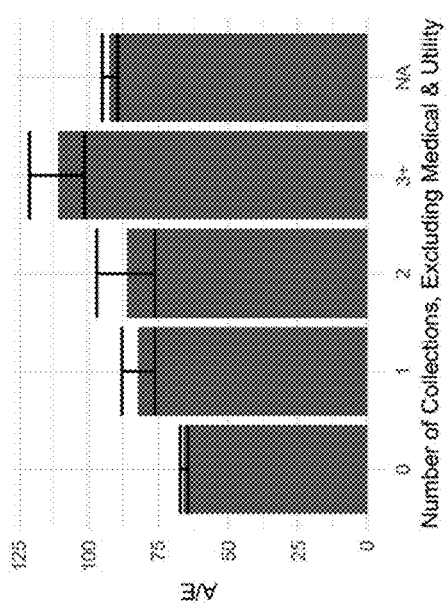
FIG. 5C displays a relationship between an individual's total number of accounts and smoking incidence, according to an embodiment.
Figure 5D:
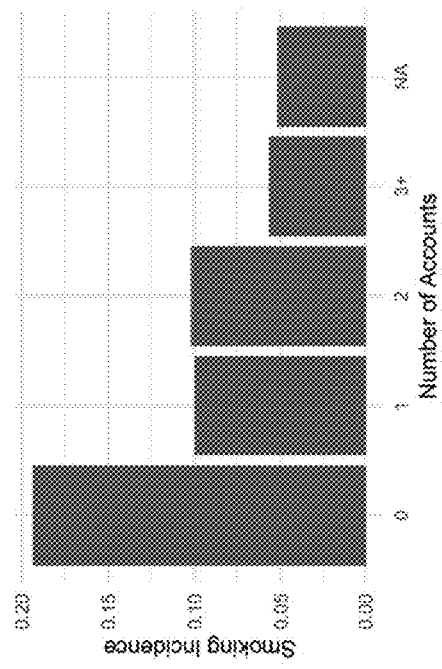
FIG. 5D displays a relationship between an individual's number of derogatory accounts and smoking incidence, according to an embodiment.

FIG. 5C and FIG. 5D show how an individual's number of derogatory public records, which include felonies, liens, bankruptcies, and evictions, and the individual's total number of accounts, are associated with smoking incidence. In FIG. 5C, an individual's total number of accounts has a negative relationship with smoking, with no accounts being associated with smoking incidence of 19.4%, 3.4 times higher than having 3 or more accounts on file, 5.7%. In FIG. 5D, number of derogatory records has a positive relationship with smoking, with one or more derogatory records being associated with 80% higher smoking incidence than having no derogatory records, 9.7% versus 5.3%. In view of significant univariate relationships between these newly acquired data attributes and target outcomes of the present fluidless protocols, an embodiment of the present disclosure builds multivariate models with protective value for mortality and smoking risk.

Initial data acquisition and pre-processing procedures (e.g., data append, missing value imputation, feature generation and exclusion) provide complete data with a sizable, though reduced, set of potential predictors for model construction. The modeling framework is designed to select model inputs from these predictors based on their joint ability to optimize a given objective function of each model in the fluidless model suite 150. This objective is model-specific, e.g., to minimize predicted mortality error or to maximize predicted likelihood of smoking. In an embodiment, the Random Forest Modeling module 130 serves as a general, reusable framework that yields relatively parsimonious models while optimizing the specific objective of each model.

Algorithm 1 presents a backward feature selection process that balances held-out performance with rapid, but principled, model development. Beginning with the superset of variables and inclusion of random noise vectors, the algorithm trains a series of models using k-fold cross-validation to generate held-out predictions to compute a model score and an averaged variable importance ranking across all variables. All variables that fall below the importance ranking of random noise are then dropped to produce the set of model covariates for the subsequent iteration. The process is repeated until the covariate list converges, and a final model is trained without the inclusion of the random variables. Corresponding pseudo code of an iterative procedure for selecting a locally minimal set of variables that yields a high-performing model is described as follows:

Algorithm 1: BackwardModelSelection(D,k,HS)
1  D←D plus random vectors R=$R_1$ ... $R_j$
2  iter←1
3  $V_0$←0
4  $V_1$←attrs (D)
5  while $V_{iter} \neq V_{iter\_1}$ do
6    model scores S←∅
7    variable importance list VI←∅
8    for hyperparameter setting hs∈HS do
9      predictions P←∅
10     for fold f in 1 to k do
11       train model $M_{hs}$ on $D_{1:k\{f\}}$ with covariate set $V_{iter}$
12       P←P∪predict ($M_{hs}$, $D_f$)
13       $VI_{f,hs}$←importance ($M_{hs}$)
14     $S_{hs}$←evaluate (P,D)
15   M←$argmin_{hs}$S
16   dropped variables DV←V>R in avg($VI_{hs}$)
17   iter←iter+1
18   $V_{iter}$←$V_{iter\_1}$\DV
19 return M In various embodiments, this procedure is applied to construction of both the Fluidless Mortality models 152, 312 and the Smoking Propensity models 154, 314.

In various embodiments, models of the fluidless model suite 150 comprise machine learning models that are trained on various sets of training data. Suitable machine learning model classes include but are not limited to: random forests, logistic regression methods, support vector machines, gradient tree boosting methods, nearest neighbor methods, and Bayesian regression methods.

In an embodiment, models of fluidless model suite 150 use one or more models 132, 134, and 136 within the Random Forests ensemble 130 for Survival, Regression, and Classification (RF-SRC). Random Forest Modeling module 130 serves as a general, reusable framework that yields relatively parsimonious models while optimizing the specific objective of each model. In Random Forests methods, ensemble learning is improved by injecting randomization into the base learning process. RF-SRC extends Random Forests methods and provides a unified treatment of the methodology for models including right-censored survival (single and multiple event competing risk), multivariate regression or classification, and mixed outcome (more than one continuous, discrete, and/or categorical outcome). When one continuous or categorical outcome is present, the model reduces to univariate regression or classification respectively.

Random forests models for classification (model 136) work by fitting an ensemble of decision tree classifiers on sub samples of the data. Each tree only sees a portion of the data, drawing samples of equal size with replacement. Each tree can use only a limited number of features. By averaging the output of classification across the ensemble, the random forests model can limit over-fitting that might otherwise occur in a decision tree model.

In an embodiment, model training used 10-fold cross validation and a grid-search of relevant hyperparameters (number of trees, minimum size of terminal nodes) for random forests.

In various embodiments, the predictive machine learning models identify features that have the most pronounced impact on predicted value. Different types of fluidless underwriting model may identify different features as most important. For example, a model based upon a mortality risk signal may identify different leading features than a model based upon a tobacco propensity signal. In various embodiments, leading model features were extracted from sources such as Public Records data 334, Credit Risk data 338, and CMI data 355.

In an embodiment, the predictive value of model features was measured using the minimal depth of a maximal subtree (7), i.e., shortest distance from the root node to the parent node of the maximal subtree, as a variable importance metric. The importance metric used conventionally for random forests is permutation-based variable importance, a time-consuming procedure. As applied within the global structure of the random forests ensemble, the minimal depth of a maximal subtree is a more efficient importance metric, which is faithful to the global structure of the model and is independent of model task and the values calculated at terminal nodes.

Variable importance metrics for random forests can exhibit biases with respect to the number of chosen splits for features with different distributions and cardinalities. In an embodiment, modeling injected random noise variables to compensate for this effect using a computationally efficient procedure. Injected random noise variables corresponded to several main categories of distributions observed in the data set: (1) normal for continuous values; (2) binary with a proportion set to the mean proportion across all binary variables; and (3) two negative binomial variables for count-based features that exhibit small and large dispersion.

FIG. 3 displays a simplified schematic of a system for evaluating program-eligible applicants for approval to receive a fluidless underwriting offer. System 300 requests inputs 320 from various third party API's 330, 340 and receives fluidless digital applications of the sponsoring enterprise. System 300 tests inputs 310 across a set of fluidless models 310 of the enterprise in order to determine whether to present an accelerated underwriting offer to the applicant. Models 310 include a comprehensive algorithmic rule system 318 and three probabilistic models 312, 314, 316. In various embodiments, in order to receive approval for presentation of an accelerated underwriting offer, the application must pass all model components 312, 314, 316, 318.

In various embodiments, for one or more of probabilistic model components 312, 314, 316, the fluidless underwriting protocol determines a quantitative risk score for the fluidless application and determines whether the respective risk score exceeds a set eligibility threshold for the respective model. For each of the model components, the system 300 incorporates eligibility thresholds established using a threshold-setting procedure. These eligibility thresholds can be important tools for actuarial analysis, i.e., for determining an observable correlation between policyholder characteristics and cost to the sponsoring enterprise. The threshold-setting procedure can determine a certain percentage of the business of a given risk class assignment to be eligible. The threshold-setting procedure can set cohort-specific thresholds by decreasing volume incrementally until a target mortality impact is reached. The threshold-setting procedure can set different thresholds for the various component models. In an embodiment, the threshold-setting procedure sets thresholds within a pre-set range of minimum and maximum risk scores.

Fluidless Algorithmic Rule System 318 stores and applies rules that reflect a comprehensive set of medical and underwriting guidelines developed by experts in underwriting and insurance medicine, but that exclude rules based on clinical laboratory data. In the present disclosure, rules applied by the Fluidless Algorithmic Rule System 318 are sometimes called "non-clinical rules." In an example, module 318 stores about 4000 non-clinical rules. Each rule determines the best available risk class in the presence of certain values in the application. For example, a high BMI would preclude an applicant from receiving a preferred-risk offer. Fluidless Algorithmic Rule System 318 executes all non-clinical rules across data retrieved from various Clinical Guidelines databases 140. In an embodiment, Fluidless Algorithmic Rule System 318 executes all non-clinical rules across data retrieved from Prescription Drug (Rx) database 342, Medical Information Bureau (MIB) database 344 and motor vehicle records (MVR) database 346.

In an embodiment, the Prescription Drugs (Rx) input 342 determines whether the application remains eligible in view of publically available information about prescription fills. Additional eligibility criteria are checked via applying the automated rules to other inputs retrieved from MIB database 344 and MVR database 346. In an embodiment, Fluidless Algorithmic Rule System 318 can "clear" an algorithmic rule if it identifies adequate cause to override information flagged by the system. In an embodiment, if one or more rules of module 318 remain "red," then the system automatically notifies the advisor assigned to the applicant to order a lab test and paramedical examination.

In building the predictive models of the present disclosure, model datasets may have populations in the hundreds of thousands or millions of individuals. In an example, Fluidless Mortality Model 312 was built from historical applications of the sponsoring enterprise containing 1.3 MM records. Data preprocessing retained applicants with no missing CMI, BMI, or public records, yielding a training set of around 230,000 historical applications 144. In an example, the Rx data set 342 constructed during model building contained data for more than 120,000 applicants, including more than three million prescription fill records.

In an embodiment, Fluidless Mortality Model 312 predicts mortality risk of a given individual relative to the individual's age and sex cohort without use of clinical data. Fluidless Mortality Model 312 seeks to identify fluidless applicants that pose the lowest mortality risk, to accelerate their experience with a simplified underwriting process. In an embodiment, in processing a fluidless application, if Fluidless Mortality Model 312 determines a mortality risk score above a predetermined level, then the system automatically notifies the advisor assigned to the applicant to order a lab test and paramedical examination.

Traditional methods of underwriting for mortality employ survival modeling for predicting ground-truth mortality. Survival modeling seeks to approximate the survival function, which describes the probability that an event, occurring at a random variable time, occurs later than some given time. In an embodiment, in lieu of employing survival modeling, Fluidless Mortality Model 312 used a regression framework 134 to predict relative mortality. Regression framework 134 was seen to avoid temporal inconsistencies with public records and credit risk attributes that would occur in using the full range of exposure in survival modeling, and enabled more efficient model development in dealing with hundreds of predictors and iterative feature selection.

In an embodiment, Fluidless Mortality Model 312 was trained using a regression framework with historical underwriting risk classes, using assigned risk classes from a retrospective study to generate mortality assumptions in the applications in training data. In order to incorporate nontraditional data sources (public records and credit risk) to measure mortality risk, an initial stage of the modeling pipeline was to ensure that any attribute used as a potential covariate in the model is actuarially justified. Using the data preprocessing steps 400 of FIG. 4, the modeling pipeline fitted a survival model 132 on solely the public records and credit risk attributes 330. The features that showed no predictive signal directly with observed deaths were excluded from subsequent steps of the modeling pipeline using regression.

To assess the performance of each regression model, the Fluidless Mortality Model 312 incorporates a mortality-impact metric that is designed to weigh actual low-risk applicants and predict low-risk applicants more heavily. In various embodiments, the fluidless underwriting protocol is primarily concerned about individuals who receive a low-risk score from Fluidless Mortality Model 312 and are likely to be accelerated underwriting-eligible, or who truly have low relative mortality. To account for this, the mortality-impact metric computes a weight, $w_i$, for each individual i such that a low prediction or true label is associated with a higher weight, causing the error associated with these individuals to have a larger penalty:

$$w_i = \frac{1}{\min(y_i, \hat{y}_i)}$$

This weight is multiplied by the difference between the prediction and the label, and the total error is taken as the square root of the mean of these weighted differences. In the present disclosure, the resulting mortality-impact metric is denoted as the mortality-impact weighted root mean-squared error (WRMSE):

$$e_w = \sqrt{\frac{\sum_k (y_i - \hat{y}_i) * w_i}{N}}$$

Smoking Propensity Model 314 addresses a challenge of the fluidless underwriting protocol, that actual knowledge of an individual's tobacco usage is a central factor in assessing mortality risk. Clinical laboratory tests detect nicotine metabolites in fluid samples, but this indicator of tobacco usage is missing in the fluidless underwriting process.

Rather than rely solely on self-reporting of tobacco usage, the fluidless modeling suite includes a Smoking Propensity Model 314 that specifically predicts tobacco usage.

In an embodiment, based on tobacco usage of the insured that is self-reported in the digital fluidless application, the accelerated underwriting offer includes the two risk classes UPNT and SPT, which are the best non-tobacco and tobacco fluidless risk classes respectively. If no tobacco usages were disclosed in the fluidless application, the conventional risk assignment would be the standard non-tobacco risk class UPNT, while if tobacco usage were disclosed in the fluidless application, the conventional risk assignment would be the standard tobacco risk class (SPT). In various embodiments, the Smoking Propensity Model 314 identifies tobacco usage by a significant portion of the unreported tobacco users that otherwise would be assigned a UPNT status, and denies these individuals accelerated underwriting. Performance testing has confirmed that the Smoking Propensity Model 314 significantly reduces adverse impacts on mortality risk of the fluidless underwriting program due to unreported tobacco usage.

In an embodiment, Smoking Propensity Model 314 defines smoking as a binary outcome. The training data set assigns the status of smoking to individuals who either had a positive nicotine test from urine or saliva or were offered a tobacco risk class. In the training data, males have a smoking status a higher rate than females across all ages. Younger males have a smoking status at a much higher rate than older males. The rate of smoking status has significantly decreased over time during the time period of the historical applications. Based on testing of various modeling methods, random forests performed comparably to, or better than, the other methods. This model class was selected for the Smoking Propensity Model 154, 314 for consistency across the fluidless model suite 150. The smoking propensity model is a classifier (using RF-C model 136) that estimates the propensity for an individual to be a smoker, i.e., for the smoking status of a particular individual to be TRUE given a set of predictors.

In various embodiments, the Smoking Propensity Model was initialized with the same set of attributes as the Fluidless Mortality Model, and was trained in two different model versions. A first smoking propensity model was trained with both credit risk and public records, while a second smoking propensity model was trained with only public records. A version of the smoking propensity model adopted as Smoking Propensity Model can be trained with both credit risk and public records. Feature selection resulted in 59 attributes. A lift curve for the Smoking Propensity Model 314 indicates that this model identifies approximately 2.5 times more smokers in the first decile than the overall baseline smoking rate.

In an embodiment, the Rx Model 316 (Prescription Fills model 156) predicts the probability of declining accelerated underwriting offer or issuing a substandard offer conditioned on information derived from prescription drug fills. In an embodiment, Rx records in training data were pulled from a third party pharmacy database vendor. The Rx data included prescribed drugs and dosages, dates filled and re-filled, therapeutic class, and name and specialty of the prescribing doctor. In addition, Rx data included a priority associated with each drug based on an analysis of each individual's prescription drug history. Priority is indicated by color labeling of red, yellow and green, with red signaling the greatest risk.

In an embodiment, given a set of Rx fills for each individual, model training generated aggregate features to characterize the full prescription drug history. These features include the overall variety and total fills of drugs (by red, yellow, and green priority), variety and total fills of recent high-risk (red) drugs, variety and total fills of opioid-related drugs, and number of physicians with specialties related to severe diseases. In addition, model training selected the top 50 generic drugs by calculating the proportion of substandards, and declines associated with each drug and ranking their importance after adjusting for the joint credibility of all drugs and their interactions using a Markov chain Monte Carlo approximation. The most important drugs are generally prescribed for diabetes, heart disease, mental health, and other serious conditions. The final set of predictors also included age, gender and BMI.

In an embodiment, random forest classifier 136 was selected for Rx Model 316. In other embodiments, Rx Model 316 incorporates a classifier based on a model class other than random forests. In an embodiment, if Rx Model 316 indicates an applicant has high risk, then the system automatically notifies the advisor assigned to the applicant to order a lab test and paramedical examination.

Figure 6:
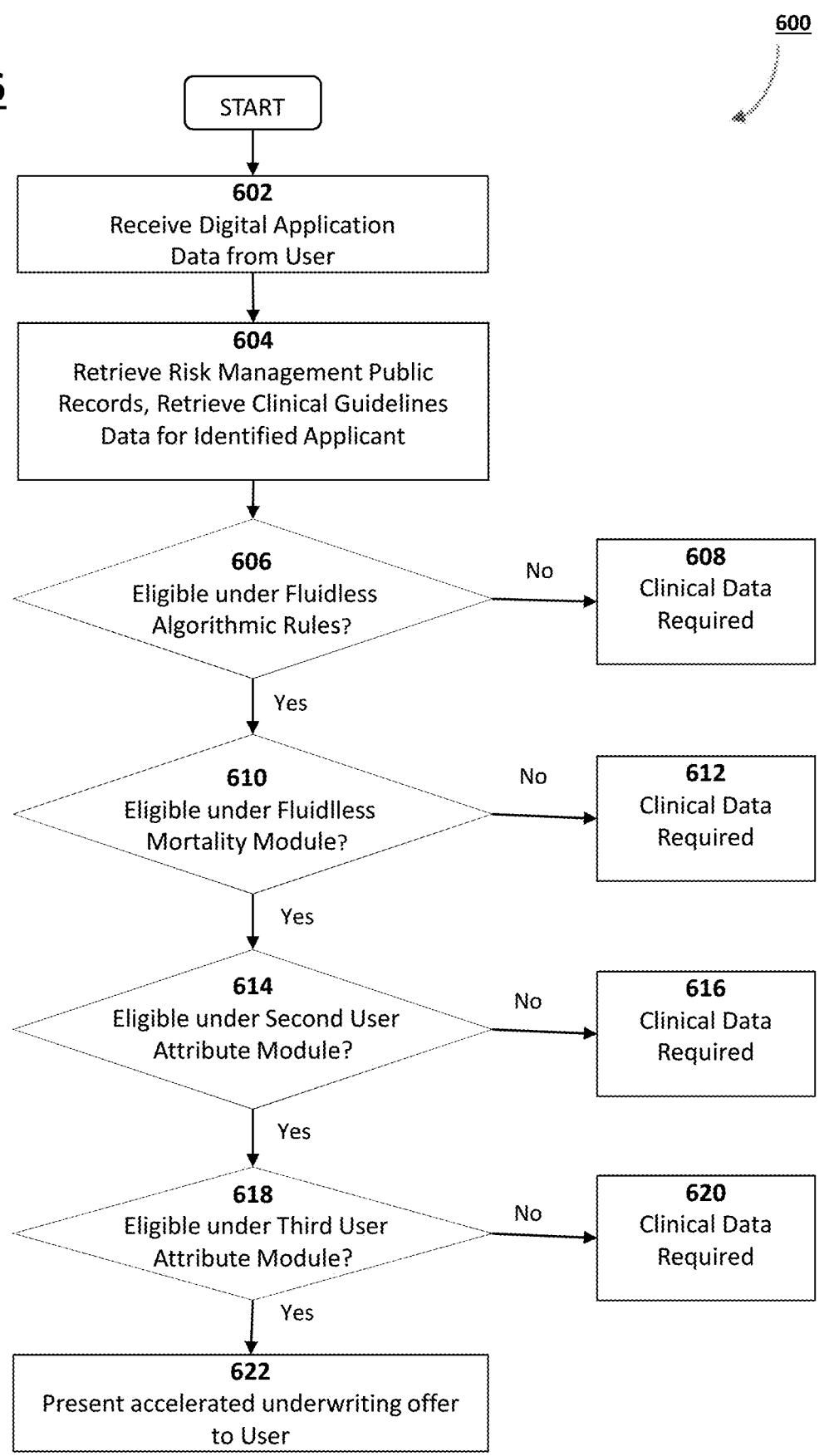
FIG. 6 is a flow chart diagram of a fluidless underwriting protocol, according to an embodiment.

In a method 600 for fluidless underwriting as shown in FIG. 6, at step 602 the fluidless underwriting system receives a fluidless digital application, e.g., from an applicant device. In an embodiment, at an initial stage of processing, the analytical engine 114 screens the application for program eligibility based on a set of program parameters. In an embodiment, program eligibility parameters include: (a) an age of the insured between 17 and 59, inclusive; (b) BMI between 18-31; (c) a maximum face amount of the insurance policy; (d) the requested life insurance product is included on a list of available products.

In an optional embodiment of step 602, if initial screening determines that an applicant meets the program parameters, to proceed with fluidless underwriting an advisor representing the sponsoring enterprise must also select the option for fluidless consideration during application submission. Advisors experienced with the criteria for eligibility for accelerated underwriting (also herein called accelerated underwriting program), can review the submitted digital application and may identify applicants that are unlikely to qualify for fluidless underwriting (e.g., if the applicant is diabetic or overweight) so as not to delay ordering clinical data.

If the application meets initial eligibility requirements, the method then retrieves 604 public records and clinical guidelines for the identified applicant. The application must pass a set of risk-related criteria to receive a fluidless offer. At step 606, the method determines eligibility of the fluidless application under Fluidless Algorithmic Rules. If the fluidless application is eligible under the Fluidless Algorithmic Rules, the process proceeds to step 610. If the fluidless application is not eligible under the Fluidless Algorithm Rules, e.g., because one or more critical algorithmic rules result in a "red" determination, the process declines 608 the accelerated underwriting offer. In an embodiment, Fluidless Algorithm Rules result in a "red" determination if any major medical risk or non-medical risk (lifestyle risk) appears on the fluidless application. In various embodiments, the process declines the accelerated underwriting offer by automatically notifying the user (applicant) via user device 170 that it is necessary to obtain a lab test and paramedical examination and/or by automatically notifying an advisor assigned to the application to order the lab test and paramedical examination.

At step 610, the method determines eligibility of the fluidless application under the Fluidless Mortality Module. If the fluidless application is found eligible by the Fluidless Mortality Module, the process proceeds to step 614. If the fluidless application is not found eligible by the Fluidless Mortality Module, e.g., because the applicant is determined to have an unacceptable mortality risk score, the process declines 612 the accelerated underwriting offer, e.g., by automatically notifying the user (applicant) that it is necessary to obtain a lab test and/or by automatically notifying an advisor assigned to the application to order the lab test and paramedical examination.

In an embodiment of step 610, the method determines eligibility of the fluidless application under the Fluidless Mortality Model by determining a mortality risk rank. As used in the present disclosure, a mortality rank can include a raw mortality score. In another embodiment, a mortality risk rank incudes a tier or group corresponding to a given mortality score, wherein the tier or group is selected from a "high risk" and "low risk" tiers or groups that are based upon a distribution of mortality risk scores for a population of new business applicants of the enterprise. In an embodiment, a mortality risk rank includes a percentile classification of a given mortality risk score relative to all mortality risk scores for a population of customers of the enterprise. In an embodiment, a mortality risk rank can include a combination of the above types of rank. Similarly, in the present disclosure other risk ranks such as "second risk rank" and "third risk rank" may include one or more of these embodiments.

At step 614, the method determines eligibility of the fluidless application under the Second User Attribute Module. In an embodiment, the Second User Risk Attribute model predicts likelihood of at least one risk factor that normally can be indicated by clinical data when included in an application. In an embodiment, the Second User Attribute Model is a Smoking Propensity Module. The Smoking Propensity Module predicts whether the applicant is a smoker or non-smoker, which normally can be indicated in clinical data included in typical medical examinations that screen for nicotine and cotinine in the urinalysis. If the fluidless application is found eligible by the Second User Attribute Module, the process proceeds to step 618. If the fluidless application is not found eligible by the Second User Attribute Module, e.g., because the applicant receives a smoking binary classification by the Smoking Propensity Module, the process declines 616 the accelerated underwriting offer, e.g., by automatically notifying the user (applicant) that it is necessary to obtain a lab test and/or by automatically notifying an advisor assigned to the application to order the lab test and paramedical examination.

At step 618, the method determines eligibility of the fluidless application under the Third User Attribute Module. In an embodiment, the Third User Risk Attribute Module predicts likelihood of at least one additional risk factor that normally can be indicated by clinical data when included in an application, wherein the additional risk factor is different from the risk factor predicted by the Second User Risk Attribute Module. In an embodiment, the Third User Attribute Model is a Prescription Fills (Rx) Module. Prescription Fills (Rx) Module can predict whether the applicant has or is at risk from various diseases and conditions that normally can be indicated in clinical data. If the fluidless application is found eligible by the Third User Attribute Module, the process proceeds to step 622. If the fluidless application is not found eligible by the Third User Attribute Module, e.g., because the applicant receives a substandard or decline classification by the Prescription Fills (Rx) Module, the process declines 620 the accelerated underwriting offer, e.g., by automatically notifying the user (applicant) that it is necessary to obtain a lab test and/or by automatically notifying an advisor assigned to the application to order the lab test and paramedical examination.

In determining eligibility of the fluidless application against multiple risk attributes, in general the order of eligibility determinations is not critical. The operations can be performed in parallel or concurrently, and the order of the operations may be re-arranged. In the method 600, the steps of determining eligibility under Fluidless Algorithmic Rules 606, determining eligibility under Fluidless Mortality Module 610, determining eligibility under Second User Attribute Module 614, and determining eligibility under Third User Attribute Module 618 may be carried out in any order or concurrently.

At step 622, having passed all criteria 606, 610, 614, and 618, the method automatically presents an accelerated underwriting offer in the fluidless digital application. In various embodiments, step 622 automatically communicates the accelerated underwriting offer to the user (applicant) via user device 170 and/or automatically notifies an advisor assigned to the application to communicate the accelerated underwriting offer to the applicant.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require, or imply, that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code, with it being understood that software and control hardware can be designed to implement the systems and methods based on the description here.

When implemented in software, the functions may be stored as one or more instructions or codes on a non-transitory computer-readable or processor-readable storage medium. The steps of a method or algorithm disclosed here may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method for processing an electronic application without clinical data, the method comprising:
    receiving, by a server, information for an electronic application from a user device, wherein the information for the electronic application excludes all clinical data for an applicant;
    upon receiving the information for the electronic application from the user display device, retrieving, by the server, public data identified with the applicant of the electronic application from one or more third party sources;
    executing, by the server, a first predictive machine learning model configured to determine a first risk rank representative of a mortality risk for the electronic application and to classify the electronic application into one of a first high risk group and a first low risk group based upon the first risk rank,
    wherein the first predictive machine learning model is trained by inputting into the first predictive machine learning model a plurality of historical application records supplemented with public data identified with an applicant of the respective historical application record, wherein the first predictive machine learning model is iteratively trained using updated public data to select variables of the public data with highest importance based on mortality risk;
    executing, by the server, a second predictive machine learning model configured to determine a second risk rank representative of a smoking propensity of the electronic application and to classify the electronic application into one of a second high risk group and a second low risk group based upon the second risk rank;
    executing, by the server, a third predictive machine learning model configured to determine a third risk rank representative of prescription drug data of the electronic application, and to classify the electronic application into one of a third high risk group and a third low risk group based upon the third risk rank; and
    responsive to the server classifying the electronic application into all of the first low risk group, the second low risk group, and the third low risk group, generating, by the server, a user interface that displays information associated with an accelerated application offer.

2. The method of claim 1, wherein the first predictive machine learning model is a regression random forest model.

3. The method of claim 1, wherein the public data identified with the applicant of the electronic application, and the public data identified with the respective applicant of each historical application record, comprise public records and credit risk data.

4. The method of claim 3, wherein the first predictive machine learning model is configured to fit a survival random forest model to the public records and the credit risk data record to select actuarially important attributes as covariates of first predictive machine learning model.

5. The method of claim 1, wherein the first predictive machine learning model is configured to fit a survival model to the public data to select attributes of the public data with highest importance based on mortality risk as variables of the first predictive machine learning model.

6. The method of claim 5, wherein the survival model is configured to approximate a survival function that describes probability that an event occurs later than some given time.

7. The method of claim 1, wherein the second predictive machine learning model comprises a random forest classification model configured to estimate a propensity of the applicant of the respective historical application record to be a smoker.

8. The method of claim 1, wherein the third predictive machine learning model comprises a prescription drug data random forest classification model configured to determine disqualifying medical risks based on information derived from prescription drug fills for the applicant of the electronic application.

9. The method of claim 1, further comprising, when the server classifies the electronic application into at least one of the first high risk group, the second high risk group, and the third high risk group, generating and presenting a user interface that displays an instruction to submit the clinical data for the applicant of the electronic application.

10. A method for processing an electronic application without clinical data, the method comprising:
    receiving, by a server, information for an electronic application from a user device, wherein the information for the electronic application excludes all clinical data for an applicant;

upon receiving the information for the electronic application from the user display device,
retrieving, by the server, public data identified with the applicant of the electronic application from one or more third party sources;
executing, by the server, a first predictive machine learning model configured to determine a first risk rank representative of a mortality risk for the electronic application and to classify the electronic application into one of a first high risk group and a first low risk group based upon the first risk rank, wherein the first predictive machine learning model is trained by inputting into the first predictive machine learning model a plurality of historical application records supplemented with public data identified with an applicant of the respective historical application record, wherein the first predictive machine learning model is iteratively trained using updated public data to select variables of the public data with highest importance based on mortality risk;
executing, by the server, a second predictive machine learning model configured to determine a second risk rank representative of a smoking propensity of the electronic application and to classify the electronic application into one of a second high risk group and a second low risk group based upon the second risk rank, wherein the second predictive machine learning model applies random forest classification to estimate the smoking propensity of the electronic application and to determine a smoking/non-smoking binary target;
executing, by the server, a third predictive machine learning model configured to determine a third risk rank representative of prescription drug data of the electronic application, and to classify the electronic application into one of a third high risk group and a third low risk group based upon the third risk rank; and
responsive to the server classifying the electronic application into all of the first low risk group, the second low risk group, and the third low risk group, generating, by the server, a user interface that displays information associated with an accelerated application offer.

11. The method of claim 10, further comprising, when the server classifies the electronic application into at least one of the first high risk group and the second high risk group, of generating and presenting a user interface that displays an instruction to submit the clinical data for the applicant of the electronic application.

12. The method of claim 10, wherein the first predictive machine learning model is configured to fit a survival random forest model to the public records and the credit risk data record to select the actuarially important attributes of the public records and credit risk data as covariates of the first predictive machine learning model.

13. The processor-based method of claim 10, wherein the first predictive machine learning model is a regression random forest model.

14. The processor-based method of claim 10, further comprising, upon receiving the information for the electronic application from a user device, of
executing the third predictive machine learning module to determine the third risk rank representative of a third user risk attribute, and to classify the electronic application into one of the third high risk group and the third low risk group based upon the third risk rank; and
when the processor classifies the electronic application into all of the first low risk group, the second low risk group, and the third low risk group, generating and presenting the user interface that displays the accelerated application offer.

15. The processor-based method of claim 14, wherein the third predictive machine learning model comprises a prescription drug data model configured to determine disqualifying medical risks derived from prescription drug fills for the applicant of the electronic application.

16. The processor-based method of claim 10, further comprising:
imputing missing values of public records and credit risk data to supplement the historical application records; and
inputting the supplemented historical application records into a random forest model ensemble.

17. The processor-based method of claim 10, further comprising:
transforming variables of public records and credit risk data to supplement the historical application records via one or more of constructing count indicator variables, calculating ratios between countervailing quantitative variables, and determining temporal rates and temporal extents of time-dependent variables; and
inputting the supplemented historical application records into a random forest model ensemble.

18. A system comprising:
an analytical engine server comprising:
a first module configured for receiving information for an electronic application from a user device that excludes all clinical data for an applicant of the electronic application, and for retrieving public data identified with the applicant of the received electronic application from one or more third party source;
a second module configured for executing a predictive machine learning module to determine a mortality risk rank for the electronic application and classify the electronic application into a first low risk group or a first high risk group,
wherein the first predictive machine learning model is trained by inputting into the first predictive machine learning model a plurality of historical application records supplemented with public data identified with an applicant of the respective historical application record, wherein the first predictive machine learning model is iteratively trained using updated public data to select variables of the public data with highest importance based on mortality risk;
a third module configured for executing a smoking propensity predictive model, wherein the smoking propensity model is configured to estimate a propensity of the applicant of the electronic application to be a smoker and determine a smoking/non-smoking binary target;
a fourth module configured for executing a prescription drug data predictive model configured to determine disqualifying medical risks based on information derived from prescription drug fills for the applicant of the electronic application; and
a fifth module configured for generating and presenting a user interface that displays information associated with an accelerated application offer when the analytical engine server classifies the electronic application into the first low risk group, determines the non-smoking binary target, and does not determine the disqualifying medical risk.

19. The system of claim 18, wherein the fifth module is further configured for generating and presenting a user interface that displays an instruction to submit the clinical data for the applicant of the electronic application when the analytical engine server effects one or more of the following: classifies the electronic application into the first high risk group, determines the smoking binary target, determines the disqualifying medical risk.

20. The system of claim 18, wherein the predictive machine learning model of the second module is a regression random forest model, and the smoking propensity model of the third module is a random forest classification model.

* * * * *